US010450254B2

(12) United States Patent
Frey et al.

(10) Patent No.: US 10,450,254 B2
(45) Date of Patent: Oct. 22, 2019

(54) METHOD FOR THE COMBINED PRODUCTION OF POLYOLS IN THE PRESENCE OF AN INORGANIC BASE

(71) Applicant: OXEA GmbH, Monheim (DE)

(72) Inventors: Guido D. Frey, Mülheim (DE); Melanie Bothe, Düsseldorf (DE); Heinz Strutz, Moers (DE); William E. Slinkard, Richmond, TX (US)

(73) Assignee: OXEA GMBH, Monheim (DE)

( * ) Notice: Subject to any disclaimer, the term of this patent is extended or adjusted under 35 U.S.C. 154(b) by 0 days.

(21) Appl. No.: 16/327,041

(22) PCT Filed: Sep. 5, 2017

(86) PCT No.: PCT/EP2017/072248
§ 371 (c)(1),
(2) Date: Feb. 21, 2019

(87) PCT Pub. No.: WO2018/077515
PCT Pub. Date: May 3, 2018

(65) Prior Publication Data
US 2019/0241492 A1   Aug. 8, 2019

Related U.S. Application Data

(60) Provisional application No. 62/412,306, filed on Oct. 25, 2016.

(30) Foreign Application Priority Data

Nov. 9, 2016  (EP) .................................... 16198007

(51) Int. Cl.
C07C 29/38   (2006.01)
C07C 31/22   (2006.01)
C07C 31/20   (2006.01)

(52) U.S. Cl.
CPC .............. *C07C 29/38* (2013.01); *C07C 31/20* (2013.01); *C07C 31/22* (2013.01)

(58) Field of Classification Search
CPC .......... C07C 29/38; C07C 31/20; C07C 31/22
See application file for complete search history.

(56) References Cited

U.S. PATENT DOCUMENTS

2016/0145179 A1\*  5/2016  Strutz ..................... C07C 29/38
568/853

FOREIGN PATENT DOCUMENTS

WO       2015020794 A1    2/2015

OTHER PUBLICATIONS

International Preliminary Report on Patentability dated Apr. 30, 2019.
International Search Report dated Nov. 9, 2017.
Written Opinion dated Nov. 9, 2017 (in German).

\* cited by examiner

*Primary Examiner* — Jafar F Parsa
(74) *Attorney, Agent, or Firm* — Michael W. Ferrell

(57) ABSTRACT

The present invention relates to a process for simultaneously consecutive preparation of polyols by base-catalyzed reaction of at least two different mid-chain aldehydes with formaldehyde. The simultaneous consecutive mode of operation makes it possible to achieve high conversions and high selectivities for both aldehydes, with additional achievement of a distinct reduction in the amount of unreacted formaldehyde remaining. This leads to improved process economics, since the energy costs for workup of the formaldehyde stream are distinctly reduced.

20 Claims, 1 Drawing Sheet

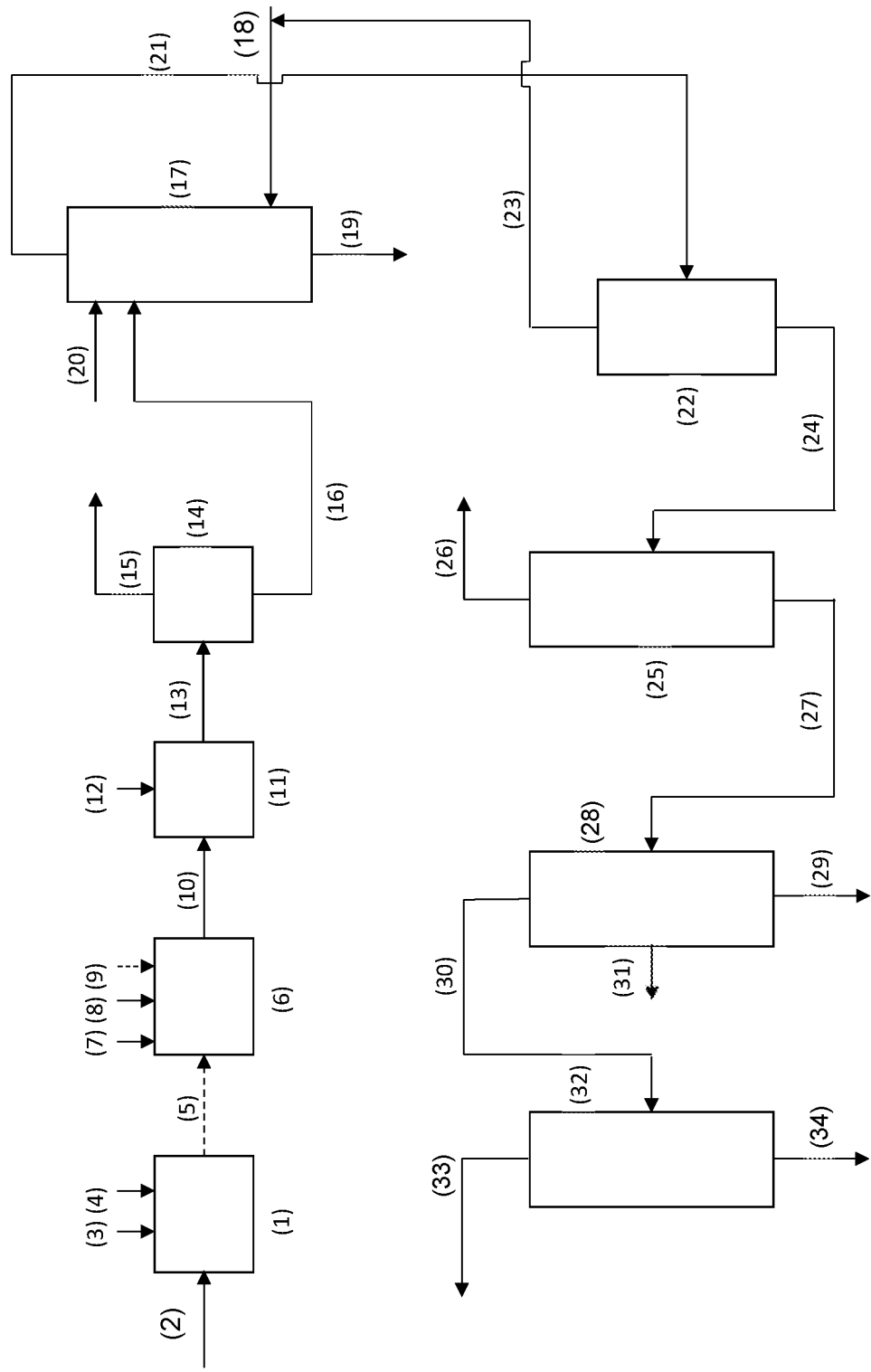

METHOD FOR THE COMBINED PRODUCTION OF POLYOLS IN THE PRESENCE OF AN INORGANIC BASE

CLAIM FOR PRIORITY

This application is a national phase entry of PCT/EP2017/072248, filed Sep. 5, 2017, which was based on provisional application U.S. 62/412,306, filed Oct. 25, 2016, and European application EP16198007.3, filed Nov. 9, 2016. The priorities of applications PCT/EP2017/072248, U.S. 62/412,306, and EP16198007.3 are hereby claimed and their disclosures are incorporated herein by reference.

TECHNICAL FIELD

The present invention relates to a process for simultaneously consecutive conversion of polyols by base-catalysed reaction of at least two different mid-chain aldehydes with formaldehyde. The simultaneous consecutive mode of operation makes it possible to achieve high conversions and high selectivities for both aldehydes, with additional achievement of a distinct reduction in the amount of unreacted formaldehyde remaining. This leads to improved process economics, since the energy costs for workup of the formaldehyde stream are distinctly reduced.

BACKGROUND

Polyhydric alcohols or polyols, such as trimethylolpropane or neopentyl glycol, have considerable economic significance as condensation components for formation of polyesters or polyurethanes, synthetic resin varnishes, lubricants and plasticizers. For this reason, various industrial methods which are supposed to lead to high-quality products at minimum expense have been developed. The emphasis of the developments lies essentially in the field of those process parameters that have a direct influence on the yield of desired main product. By contrast, there is no overall assessment of the polyol yield with simultaneous consideration of the efficiency of the overall reactant and energy input.

One possible preparation route for obtaining polyols includes the reaction of aldehydes with formaldehyde in aqueous solution. By the aldol addition mechanism, the aldehyde can at first form a methylol derivative of the corresponding aldehyde with formaldehyde in a first step. This addition reaction can be effected, for example, in the presence of catalytic amounts of bases or acids. Subsequently, in a second step, the aldehyde group can be reduced to the alcohol group with excess formaldehyde and with stoichiometric amounts of a base in a Cannizzaro reaction. In that case, a by-product formed at the same time is a stoichiometric amount of the formate of the added base. The corresponding formate salts are obtained as by-products and can be used, for example, as deicing agents, drilling aids or as auxiliaries in the leather industry.

For this basic reaction type, there are various different approaches to a solution in the patent literature relating to the preparation of polyols.

For example, the preparation of trimethylolpropane by an inorganic Cannizzaro process is disclosed in DE 1 182 646 A, WO 99/20586 A1, EP 2 341 041 A1, EP 1 323 698 A2, WO 2015/020796 A1 or WO 2015/020794 A1. The underlying reaction between n-butanal and formaldehyde is highly exothermic, and the heat released leads to disadvantageous temperature peaks which can affect the selectivity of the reaction and lead to colour problems in the end product. The reaction is typically conducted in the presence of a large amount of water with a correspondingly high heat capacity, in order to absorb the heat of reaction. A large amount of water is achieved through the use of a comparatively dilute aqueous formaldehyde solution, and through the use of aqueous solutions of inorganic bases.

According to DE 1 182 646 A1, it is likewise advantageous to use a high excess of formaldehyde in order to increase the yield of trimethylolpropane and to suppress the formation of unwanted by-products which can lead to colour impairments. Based on the n-butanal input, it is stated that it is possible to work with 6 to 10 moles of formaldehyde. It is also recommended that the inorganic base be used in an amount exceeding the amount theoretically required.

A mode of preparation with gradual addition of the reactants is disclosed, for example, in WO 2015/020796 A1. For preparation of trimethylolpropane, a reaction control in a tubular reactor is proposed, in which further co-reactants are added stepwise along the tubular reactor as the reaction progresses. At the same time, the tubular reactor is supplied with a formaldehyde-containing stream, and n-butanal and an aqueous solution of an inorganic base are added at various points in the tube over the length of the tubular reactor. The stepwise addition of n-butanal to the formaldehyde-containing stream constantly ensures a high excess of formaldehyde, based on n-butanal, and promotes selectivity in the trimethylolpropane direction. At the points where n-butanal and inorganic base are added, the tubular reactor may have static mixers or internals, in order to intensify the mixing after entry of the co-reactants and to remove the heat of reaction.

The known processes for preparing polyols by the Cannizzaro process in the presence of inorganic bases work with a considerable excess of formaldehyde, which is usually supplied to the reaction in the form of a dilute aqueous solution. After the reaction, therefore, a considerable amount of unreacted formaldehyde has to be removed from the crude product mixture. As a result of the high proportion of water, formaldehyde is removed as a highly dilute aqueous solution, for which a correspondingly high expenditure of energy is required.

SUMMARY OF THE INVENTION

It is an object of the present invention to provide an improved preparation process which allows reduction in the energy input for removal of aqueous formaldehyde solution from the crude reaction product obtained, with high space-time yields of polyols.

The object is achieved in accordance with the invention by a process for simultaneously consecutive preparation of at least two different polyols by reaction of aliphatic aldehydes with formaldehyde in the presence of an inorganic base, wherein, in a 1st process step, an aliphatic C2-C9 aldehyde is reacted with formaldehyde in the presence of an inorganic base and, without workup of the reaction solution, in a 2nd process step, the reaction solution from the 1st process step is converted further with addition of at least one aliphatic C2-C9 aldehyde other than the aldehyde from the 1st process step. It has been found that, surprisingly, this two-step process control in which the two aliphatic aldehydes are reacted at the same time (simultaneously) but successively (consecutively) allows the desired polyols to be obtained with a high conversion and a high selectivity. In addition, it should be emphasized that the coupling of the synthesis stages additionally distinctly reduces the residual contamination of the water of reaction at the end of both steps with formaldehyde. Specifically the latter leads to a distinct rise in process economy, since the energy expenditure for recovery of the formaldehyde from the aqueous solution after the reaction is distinctly reduced. This process control is additionally usable in a flexible manner, it being possible to obtain high space-time yields even in a wide variety of different reactor types, either within a continuous preparation or within a batch preparation. Moreover, the reaction mixture that flows out of the first reaction step already contains a considerable amount of water, and the risk of formation of temperature peaks in an exothermic reaction in the second process step is distinctly lowered as a result. Any input of water additionally needed within the second process step can therefore be distinctly reduced. These advantages were not to be expected from the outset overall, since the reactions in the individual process steps are each complex reactions, with a presumably high influence of further synthesis components on the individual degree of conversion, the selectivity and the by-product profile. The fact that specifically the reaction of the two different aldehydes proceeds in a comparatively independent manner, with substantial conversion of the formaldehyde reaction component, was surprising by virtue of the different reactivities and solubilities of the aldehydes in the reaction medium and because of possible cross-reactions between the two aldehydes or conversion products of the aldehydes with one another or with aldehyde still present.

Using the example of the preparation of trimethylolpropane and neopentyl glycol from n-butanal and i-butanal, one possible configuration of the reaction control is as follows:

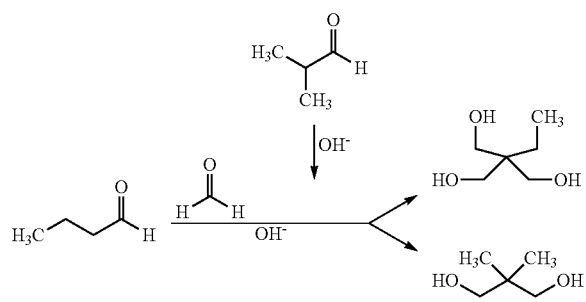

The process of the invention is based on a simultaneously consecutive preparation of at least two different polyols. This means, more particularly, that the preparation of the polyols is not conducted independently; instead, one reactant aldehyde is first reacted with formaldehyde within one reaction and, at a later juncture, at least one second aldehyde is added to the overall reaction mixture of the first aldehyde, i.e. an essentially sequential or simultaneously consecutive reaction control. At least within one period of time, both a conversion of one and of the other aldehyde take place in the reaction solution. The reaction of the different aldehydes is thus effected at least partially simultaneously and within the same reaction solution. Moreover, the juncture of simultaneous conversion is, in particular, not at the start of conversion of the first aldehyde. Reactions in which 2 different aldehydes are present as co-reactants of formaldehyde in significant amounts in a reaction solution from the outset, or in which a total amount of two different aldehydes is added together to a solution alongside the formaldehyde, i.e. essentially a simultaneous reaction of the two aldehydes with formaldehyde, are not within the scope of the invention. Nor is it within the scope of the invention when a first aldehyde includes small residual amounts of a second aldehyde and the two are simultaneously reacted with formaldehyde. The process of the invention affords significant amounts of each of two different polyols. The amounts of the two different polyols prepared are each significant when they are, for example, roughly equal or when the molar ratio between these at the end of the second process step is greater than or equal 20%, preferably greater than or equal 50% and further preferably greater than or equal 80%.

Within the process of the invention, at least two different polyols are prepared. The polyols preparable especially have at least two OH groups. The chemical composition of the polyols is of course a function of the aldehydes used and of the degree of reaction within the aldol addition and subsequent Cannizzaro reaction. Possible polyols obtainable by this process are, for example, pentaerythritol, 1,1,1-tris(hydroxymethyl)ethane (TME), 1,1,1-tris(hydroxy-methyl)propane (TMP), 1,1,1-tris(hydroxmethyl)butane (TMB), 1,1,1-tris(hydroxymethyl)-pentane, 1,1,1-tris(hydroxymethyl)hexane, 1,1,1-tris(hydroxymethyl)heptane, 1,1,1-tris-(hydroxymethyl)octane, 1,1,1-tris(hydroxymethyl)-2-methylpropane, 1,1,1-tris(hydroxymethyl)-2,2,4-trimethylpentane, neopentyl glycol, 2-propylpropane-1,3-diol, 2-methyl-2-propylpropane-1,3-diol, 2-ethyl-2-methylpropane-1,3-diol, 2-butyl-2-ethylpropane-1,3-diol, 2-butyl-2-methylpropane-1,3-diol, 2-pentylpropane-1,3-diol, 2-hexyl-2-methylpropane-1,3-diol, 2-hydroxymethyl-2-(1,3,3-trimethylbutyl)propane-1,3-diol, dimethylbutyl)-2-methylpropane-1,3-diol.

In the reaction of the invention, at least two different aliphatic aldehydes are used as well as formaldehyde. This means that at least two chemically different aldehydes are reacted with formaldehyde, where the aldehydes may in principle be different in terms of their empirical formula and/or in terms of their steric configuration. Aliphatic aldehydes are reacted, i.e. aldehydes which, as well as the aldehyde group, also bear nonaromatic hydrocarbon groups. The nonaromatic groups may especially be substituted or unsubstituted C1-C8 hydrocarbon chains. Substituted hydrocarbon chains are understood to mean hydrocarbon chains in which not more than 2 hydrogen atoms have been exchanged by heteroatoms such as 0, halogens, N or the heteroatom groups containing one of these heteroatoms that are familiar to those skilled in the art.

The two different aldehydes are reacted with formaldehyde. Appropriately, the reacting can be effected by adding an aqueous formaldehyde solution. The formaldehyde content in the aqueous solution may be 5% to 50% by weight, preferably 8% to 35% by weight and especially 9% to 30% by weight.

The reaction of the aldehyde with formaldehyde takes place in the presence of an inorganic base. Suitable inorganic bases are especially basic alkali metal or alkaline earth metal compounds, which can be added to the reaction solution as an aqueous solution or as an aqueous suspension.

In the 1st process step, an aliphatic C2-C9 aldehyde is reacted with formaldehyde in the presence of an inorganic base. C2-C9 aldehydes usable in this reaction are, for example, aliphatic n-aldehydes or branched aliphatic aldehydes. Preferably, however, it is especially possible to use acetaldehyde, propanal, n-butanal, i-butanal, valeraldehyde, 2-methyl-butanal, 3-methylbutanal, n-hexanal, 2-methylpentanal, n-heptanal, 2-methylhexanal, n-octanal, 2-ethylhexanal, n-nonanal, 2-methyloctanal, 3,5,5-trimethylhexanal, 2,5,5-trimethylhexanal. These aldehydes form the organic phase, and—without being bound by theory—contact with or diffusion into the aqueous phase results in an aldol addition with the formaldehyde present therein under catalysis by the dissolved or dispersed base. The reacting may include reaction of at least 10, 30, 50, 75 or 100 mol % of the aliphatic aldehyde in the 1st process step. It is thus possible to run the reaction to a complete or partial conversion of the aldehyde for the 1st process step. Preferably, however, at the end of the 1st process step, 5, 15, 20, 40, 60 mol % of the aldehyde used is still present in solution. The aldehyde added in the 1st process step can be added to the reaction solution all at once, divided into several stages, or continuously.

The reaction solution obtained in the 1st process step is subsequently, without workup of the reaction solution, fed directly to the 2nd process step. In this coupled reaction control, the reaction mixture flowing out of the 1st process step thus serves as the feed stream for the 2nd process step. More particularly, this means that the reaction solution from the 1st process step is fed to the 2nd process step without any further thermal, chemical or mechanical separation or processing operations, i.e. especially without distillation, settling or the like. Thus, more particularly, no further substances are taken from the reaction solution between the two process steps. If the two process steps are conducted in different reactors, transfer, for example by pumping of the reaction solution, from one reactor into another is, however, possible.

In the 2nd process step, the reaction solution from the 1st process step is reacted further at least with addition of a C2-C9 aldehyde different from the aldehyde of the 1st process step. Preferably, in the second reaction step, it is possible to use aldehydes branched in position 2, for example i-butanal. The 2nd process step thus starts, by definition, at the juncture at which a further, different C2-C9 aldehyde is added to the reaction solution from the 1st process step. In principle, aldehydes used for the 2nd process step may be the same aldehydes as described further up, but with the proviso that the aldehydes used for the 1st and the 2nd process step are different. As well as the aldehydes, in the 2nd process step, it is also possible to add further substances, for example further base or else formaldehyde. Within the 2nd process step, the newly added aldehyde and the as yet unconverted aldehyde from the 1st process step then react with the remaining (or optionally newly added) formaldehyde to form a further, different polyol. Preferably, the reaction is controlled in such a way that full conversion is achieved for both aldehydes.

In a first preferred embodiment, in the 1st process step, an aliphatic C2-C9 aldehyde unbranched in the 2 position can be reacted, and, in the 2nd process step, an aliphatic C2-C9 aldehyde branched in the 2 position. It has been found to be particularly favourable when the process control is chosen such that, in the 1st process step, an aldehyde unbranched in the 2 position is used and, in the 2nd process step, the iso form of the same or another aldehyde which is branched in the 2 position. This addition allows particularly high selectivities and conversions to be attained. In addition, it is appropriately possible to control the reaction such that two alcohols of different functionality are obtainable as main products.

In particularly high yields and without the formation of significant by-products, it is possible to obtain at least 2 different polyols, with the majority of the alcohols formed consisting of di- and triols. In a further-preferred process variant, the aldehyde added in the 1st process step can be converted to a trivalent alcohol and the aldehyde added in the 2nd process step to a divalent alcohol.

In a second preferred configuration, the aldehyde used in the 1st process step may be selected from the group consisting of n-propanal, n-butanal, valeraldehyde, and the aldehyde used in the 2nd process step may be i-butanal. Especially the coupled conversion of a straight-chain n-aldehyde in the 1st process step with an aldehyde branched in the 2 position to the aldehyde group in the 2nd process step can lead to a particularly effective process control with a relatively small number of unwanted coproducts.

Within a further aspect of the process of the invention, the 1st and 2nd process steps can be conducted at a temperature of greater than or equal 10° C. and less than or equal 105° C. In spite of the use of chemically different aldehydes and the complex interplay of the reactants within a common reaction solution, it has been found that, surprisingly, the coupled reaction can be conducted within a common, above-specified temperature range. Within this temperature range, adequate conversions can be achieved with sufficient selectivities for both aldehydes, such that the overall conversion of aldehydes is achieved with a good space-time yield. The 1st process step in particular can be conducted at a temperature of greater than or equal 20° C. and less than or equal 65° C., and the 2nd process step at a temperature of greater than or equal 30° C. and less than or equal 75° C. Within this relatively narrow range, it is possible to achieve particularly high space-time yields even for a wide variety of different reactor types.

In a further, advantageous aspect of the process of the invention, in the 2nd process step, it is additionally possible to add an inorganic base to the reaction solution. To obtain high conversions and selectivities, it has been found to be particularly advantageous that not the entire amount of base for the coupled reaction is added within the 1st process step; instead, a portion of the base required to complete the reaction is not added until the 2nd process step. This can increase the selectivity of the 1st process step, since the total amount of base in the 1st process step can be kept lower. This process control additionally enables the use of smaller amounts of water overall, since the base can be added in a more concentrated solution in the 2nd process step. Thus, the total amount of water added can be reduced, which can contribute to improved process economics.

In a further embodiment, it is possible to use the same inorganic base in the 1st and 2nd process step. In spite of the different reactivities of the different aldehydes and the different process conditions in the conversion in the 1st and 2nd process step, it has been found to be possible and suitable to conduct the reactions with the same inorganic base. By means of this process control, it is possible to obtain good selectivities and good conversions, and the use of just one base additionally facilitates the subsequent separating operations for purification of the main products and by-products.

In a further configuration of the process, the inorganic base may be selected from the group consisting of NaOH, KOH, Ca(OH)$_2$ or mixtures thereof. The group of inorganic bases cited, in the context of the process control of the invention, leads to high product conversions and selectivities. Moreover, because of the solubility of these bases, it is also possible to optimize the water content of the reaction solution, such that a smaller amount of water is obtained overall after the reaction. Preferably, it is possible to use the same inorganic base in the first and second reaction stages. Since a large amount of water is already present in the second process step, the inorganic base can be used in a comparatively high concentration. Aqueous solutions or suspensions having a concentration of 15% to 52% by weight, preferably of 30% to 50% by weight, of inorganic base have been found to be useful. It is appropriate to use commercially available aqueous solutions of inorganic base with correspondingly high concentration. Particularly suitable are aqueous potassium hydroxide or sodium hydroxide solutions or an aqueous suspension of calcium hydroxide.

In an additional aspect of the process, the molar ratio of inorganic base to aliphatic aldehyde in the two process steps may be greater than or equal 1:1 and less than or equal 1.6:1. In spite of the active alteration of the reaction solution by further addition of another aldehyde within the 2nd process step, it has been found that it is advantageously possible to choose the concentration of base at approximately the same level within the two process steps. This concentration of base leads to an adequate efficiency of both component reactions with high space-time yields, and enables a simple process control with only low energy costs for workup of the reaction solution.

Within a further process variant, the formaldehyde can be added in the 1st process step in the form of an aqueous formaldehyde solution having a formaldehyde content of greater than or equal 5% by weight and less than or equal 50% by weight. The addition of the formaldehyde in the form of an aqueous solution enables, as well as the provision of a biphasic reaction system, also effective temperature control of the reaction in the 1st process step. As a result of the heat capacity of the water, it is possible in this concentration range of formaldehyde to achieve an adequate level of conversion with simultaneous assurance of an adequate reaction rate and only low by-product formation. Advantageously, in the 1st process step, it is possible to use a 10% to 40% by weight or further preferably a 15% to 25% by weight formalin solution.

In a further configuration of the invention, the molar ratio of formaldehyde to aliphatic aldehyde in the 1st process step may be greater than or equal 3.1:1 and less than or equal 12:1, and the molar ratio of formaldehyde to aliphatic aldehyde in the 2nd process step greater than or equal 2.1:1 and less than or equal 7:1. A high molar excess of formaldehyde based on the aldehyde added in the 1st process step can distinctly favour the selectivity of the conversion of the aldehyde to a polyol. If what is desired is to prepare a trivalent alcohol particularly from the aldehyde added in the 1st reaction step, it is possible to work in the first reaction stage at above the amount required in stoichiometric terms of 3 moles of formaldehyde, with 4 to 12 and preferably with 5 to 10 moles of formaldehyde, based on 1 mol of aldehyde. In a preferred configuration, it is possible to use an aqueous formaldehyde solution in a concentration of 9% to 30% by weight and in an amount of 5 to 10 moles, based on one mole of aldehyde used in the 1st process step.

In a further configuration of the process, the formaldehyde can be added only in the 1st process step. To control the temperature of the exothermic reaction in the 1st process step and to obtain a conversion of maximum selectivity, it may be advisable to add the entire amount of formaldehyde required for the 1st and 2nd process steps at the early stage of the start of the 1st process step. In this configuration, a rapid conversion is obtained with high conversions of the first aldehyde, with the possibility of very efficient formation particularly of polyvalent alcohols having 3 OH groups. The amount of water introduced with the formaldehyde can additionally effectively reduce the level of side reactions, which can occur in view of temperature spikes. Moreover, in this process variant, through the use of the further aldehyde only in the 2nd process step, a very effective reduction in the residual formaldehyde from the 1st process step can be achieved. The reaction of the aldehyde added in the 1st process step can thus be controlled via the high molar excess of formaldehyde. Appropriately, the aldehyde added in the 2nd process step can be depleted with high efficiency, with consumption of the residual formaldehyde content (or a portion thereof), to give a polyol having a relatively low number of OH groups. Given suitable choice of the total amount of formaldehyde, this is associated with minimization of the formaldehyde recycling, including minimization of the water to be removed in the workup.

Within a further aspect of the process of the invention, the addition of at least one reactant in the 1st and/or 2nd process step can be effected stepwise. To control the selectivity of the reactions of the individual aldehydes, it may be found to be favourable when at least one of the reactants is added stepwise to the reaction solution. Stepwise addition is effected especially when the composition of the reaction solution in the 1st process step is not constant; instead, the concentration of one of the reactants in the 1st process step is increased relative to the other reactants as a function of time. For example, this can be effected by adding one of the reactants to the reaction solution in two or more stages or portions. The addition can be effected at the same site but at different times, or at different sites at different times. In this manner, it is possible to influence the reaction equilibrium and control the selectivity and conversion level of the reaction.

In a further preferred embodiment, the aliphatic aldehyde can be added stepwise to the reaction mixture in the 1st process step. Specifically the stepwise use of the aldehyde within the 1st process step can lead to a higher selectivity and decrease in the formation of unwanted by-products. This may possibly be because of improved constancy of temperature, since the stepwise introduction makes the conversion more controlled and avoids temperature spikes.

In a preferred configuration of the process of the invention, the conversion of aldehyde in the reaction mixture at the end of the 1st process step may be greater than or equal 50%. In this configuration, the 2nd aldehyde is thus not added in the 2nd process step until the conversion of the 1st aldehyde from the 1st process step is already at least 50%. In this way, a substantial portion of the formaldehyde has already been depleted and the 2nd aldehyde and the remainder of the 1st aldehyde added in the 1st process step react in a reaction solution having distinctly lower concentrations of formaldehyde. This can influence the selectivity of the reactions, and the effect of this may especially be that the residual content of the formaldehyde in the reaction solution at the end of the 2nd process step can be controlled very accurately. This process variant can lead to particularly low workup costs for the finished reaction solution. In addition, an already high conversion level in the 1st process step can reduce the amount of water and heat to be introduced into the system additionally.

In a further embodiment, the reacting in the 1st and 2nd process steps can be effected in one or more separate reactors, the reactors being selected from the group consisting of tubular reactors, shell and tube reactors, plate reactors, stirred tanks or a combination thereof. These reactor types enable particularly good thermal control of reaction by virtue of their specific heat exchange area, particularly enabling high cooling outputs per reaction section. In addition, these reactors enable good mixing to obtain high Reynolds numbers, and very homogeneous residence time characteristics of the reaction mixture.

Within an additional aspect of the invention, the reactant volume throughput per unit reactor volume and time (V/Vh)

in the two process steps may be greater than or equal 0.3 and less than or equal 4.0. This mode of operation can contribute to adequate product conversion and to a reduction in the plant costs.

In a further configuration, it is possible to use aldehydes with the same element composition in the two process steps, the aldehyde added in the 1st process step being a structural isomer of the aldehyde added in the 2nd process step.

In a further embodiment, it is possible to use aldehydes having the same element composition in the two process steps, the aliphatic aldehyde added in the 1st process step being a structural isomer of the aldehyde added in the 2nd process step, and the aldehyde added in the 1st process step being an aldehyde unbranched in the 2 position and the aldehyde added in the 2nd process step being an aldehyde branched in the 2 position. It is possible with preference to use n-butanal and i-butanal.

In a further configuration of the process, the reaction can be operated under flow conditions which are either in the transition region between laminar and turbulent flow or in the turbulence regime. This flow region has been found to be very suitable for assuring effective control of temperature in the two reactions in the two process steps. This can have a positive effect on the profile of by-products and the amount of by-products. Moreover, this flow region seems to provide a suitable phase interface which substantially avoids cross-reactions between the two aldehydes.

BRIEF DESCRIPTION OF THE DRAWINGS

Further details, features and advantages of the subject-matter of the invention are apparent from the dependent claims and from the description of the FIGURE and the accompanying examples which follows. The FIGURE shows:

FIG. 1 a schematic of a possible apparatus configuration of the process of the invention using the example of a joint preparation of trimethylolpropane and neopentyl glycol

DETAILED DESCRIPTION

Apparatus Construction for Synthesis of the Compounds

FIG. 1 shows a possible construction scheme for the coproduction of trimethylolpropane and neopentyl glycol in two reaction zones. The two reaction zones are operated with coupling to one another, the reaction mixture from the first reaction zone serving as feed stream for the second reaction zone. In addition, a further possible route for the subsequent workup of the trimethylolpropane- and neopentyl glycol-containing reaction mixture is also indicated.

The first reaction zone (1) is supplied via the line (2) with an aqueous formaldehyde-containing feed stream, via the line (3) with n-butanal, and via the line (4) with an aqueous solution of an inorganic base such as sodium hydroxide or potassium hydroxide. The conversion can be effected at temperatures of 30 to 60° C., preferably of 40 to 55° C.

Subsequently, the reaction mixture can be added to a second reaction zone (6) without further workup. The first and second reaction zones can optionally be connected via the line (5), shown by a dashed line. However, it is also possible to combine the first and second reaction zones in a multizone reactor. As well as the reaction mixture conducted in from the first reaction zone, the second reaction zone can be supplied via line (7) with i-butanal, and via line (8) with the aqueous solution of the inorganic base. Optionally, via the line (9), shown by a dashed line, an aqueous formaldehyde solution can be added to the second reaction zone (6).

The second reaction zone can be operated at a temperature of 40 to 70° C., preferably of 45 to 65° C., for formation of neopentyl glycol, and with utilization of the formaldehyde already present and of any formaldehyde added. The alkaline reaction mixture flows out of the second reaction zone through line (10) into a vessel (11) in which it is adjusted to a pH of 4 to 7 by addition of acid. The addition of acid, for example the addition of formic acid or acetic acid, is via line (12). Subsequently, the acid-treated mixture is passed via line (13) to a distillation unit (14) for removal of the excess formaldehyde in the form of a dilute aqueous solution. The distillation unit (14) may, for example, be a conventional distillation column. Possible bottom temperatures are from 80 to 160° C. and possible system pressures from 300 hPa to 0.3 MPa. The aqueous formaldehyde solution can be drawn off overhead (line (15)). At the bottom, via line (16), a concentrated aqueous solution comprising the formate, the inorganic base and likewise the desired neopentyl glycol and trimethylolpropane products is obtained. This solution can then be passed to the upper section of the extraction column (17). In the base region of the extraction column (17), the extractant can be introduced via line (18), which flows in the direction of the column head counter to the aqueous product-containing solution applied. At the base of the extraction column (17), the aqueous phase laden with the formate of the inorganic base flows away via the line (19). Appropriately, above the application point for the product-containing aqueous solution introduced via line (16), water is additionally applied to the extraction column via line (20), in order to complete the removal of formate. For removal of the extractant, the product-laden extractant can be passed via line (21) to a distillation unit (22), for example a vaporization column. Here, the extractant can be drawn off overhead and, via line (23), combined with fresh extractant introduced via line (18), and they can be returned together to the extraction column (17). Via the bottom of the distillation unit (22), the trimethylolpropane- and neopentyl glycol-containing crude mixture is removed via line (24) and separated into the individual products of value in a three-stage distillation sequence.

Apparatus Construction for Separation of the Products

For separation of the individual products, the crude product is applied to the middle section of a first distillation unit (25), which serves for low boiler removal, and from which low boilers such as residues of extractant, water and volatile by-products, such as 2-ethyl-1,3-propanediol, 2-ethyl-2-methyl-1,3-propanediol and a monocyclic formal of trimethylolpropane, are removed at the top via line (26). The first distillation unit (25) can be configured, for example, as a packed column having 10 to 25 theoretical plates and is operated, for example, at bottom temperatures of 135 to 150° C. and at pressures from standard pressure up to 60 hPa. The bottoms output from the first distillation unit is then guided via line (27) to the middle section of a second distillation unit (28) which serves to remove high boilers. The second distillation unit can be configured, for example, as a packed column and can be operated at bottom temperatures of 200 to 330° C. and reduced pressures of 10 to 90 hPa. Via line (29), the high boiler-containing bottoms stream is removed, which can be utilized in a thermal manner, for example. At the top, a mixture of neopentyl glycol and intermediate boilers having a lower boiling point than trimethylolpropane is obtained, and they are removed via line (30). Purified trimethylolpropane is withdrawn from the second distillation column (28) via the sidestream (31) and has a content of at least 95% by weight. The top product removed from the second distillation unit via line (30) is then passed to the middle section of a third distillation unit (32). Purified neopentyl glycol is removed via the line (33), while the intermediate boilers likewise supplied to the third distillation column, having a higher boiling point than neopentyl glycol, are discharged via line (34). The third distillation unit can be configured, for example, as a fractionating column or as a dividing wall column having 40 to 70 theoretical plates, and works at temperatures of 210 to 270° C. and within a pressure range of 600 hPa up to a gauge pressure of 0.2 MPa. The stream of matter withdrawn via line (33) has a neopentyl glycol content of at least 97% by weight.

In accordance with the equivalents specified in Table 1, a flask was initially charged with an aqueous formaldehyde (FA) solution, and n-butanal and KOH (45% solution) were added uniformly over a period of 10 minutes while stirring. By means of an internal thermometer, the reaction temperature is monitored and, if required, kept at the reaction temperature specified with a cold bath (water/ice mixture). After the reaction time specified in Table 1, the reaction is ended by means of addition of formic or acetic acid and adjusted to a pH of 6. The respective reaction conditions and the results of the product analysis are listed in Table 1.

TABLE 1

| | | | | | Example | | | | |
|---|---|---|---|---|---|---|---|---|---|
| | | | 1 | 1.1 | 2 | 3 | 3.1 | 4 | 5 |
| Reactor | | | | | | Flask | | | |
| FA | (% by wt.) | | | 16 | | | 36 | | 25 |
| FA | eq. | | 6.6 | 6.6 | 3.2 | 6.6 | 6.6 | 6.6 | 6.6 |
| KOH | eq. | | | 1.1 | | | 1.8 | 1.8 | 1.05 |
| n-Butanal | eq. | | | | | 1 | | | |
| Reaction time | [h] | | 0.5 | 1 | 0.5 | 2 | | 1 | |
| T | [° C.] | | 50 | 60 | 50 | 60 | 50 | 60 | 50 |
| Stopping via addition of | | | | | CHOOH | | | CH3COOH | CHOOH |
| Product analysis by gas chromatography (% by weight) | | | | | | | | | |
| Methanol | | | 3.51 | 3.24 | 1.3 | 3.04 | 8.68 | 11.71 | 2.92 |
| i- + n-Butanal | | | 0.10 | 0.02 | 0 | 0 | 0.07 | 0.03 | 0.02 |
| Secondary components | | | 1.58 | 2.57 | 3.4 | 2.51 | 2.98 | 4.1 | 2.51 |
| TMP | | | 90.37 | 88.28 | 83.3 | 84.89 | 80.47 | 76.63 | 86.3 |
| Formates + intermediate fractions | | | 0.92 | 2.46 | 4.2 | 1.39 | 1.44 | 3.04 | 2.17 |
| Ditrimethylolpropane | | | 0.65 | 0.58 | 5.3 | 0.63 | 0.61 | 1.94 | 0.35 |
| Linear bis-TMP formal | | | 0.52 | 0.60 | 2.3 | 4.43 | 3.93 | 2.01 | 2.55 |
| High boilers | | | 2.35 | 2.25 | 0.2 | 3.11 | 1.82 | 0.54 | 3.18 |
| TMP selectivity (%) | | | 93.3 | 91.1 | 84.4 | 87.3 | 87.8 | 86.6 | 88.7 |

EXAMPLES

The advantages of the process of the invention are shown by a coupled conversion of n-butanal (n) and i-butanal (i) to, respectively, trimethylolpropane (TMP) and neopentyl glycol (NPG). The examples have been broken down, inter alia, as a function of the addition, the process control (continuous vs. batch) and the reactor type used:

| Example | Process step | Product | Reactant (butanal) | Addition of reactants/process/reactor |
|---|---|---|---|---|
| 1-5 | 1 | TMP | n | Individual substance/batch/flask |
| 6-10 | 2 | NPG | i | Individual substance/batch/flask |
| 11 | 1 + 2 | TMP + NPG | n and i | Mixture/batch/flask |
| 12-14 | 1 + 2 | TMP + NPG | n and i | Separate/continuous/stirred tank cascade |
| 15-18 | 1 + 2 | TMP + NPG | n and i | Separate/batch/flask |
| 19-22 | 1 + 2 | TMP + NPG | n and i | Separate/continuous/tube |

I. Examples 1-5—Individual Batchwise Preparation of TMP (Flask)

The Cannizzaro reaction for preparation of trimethylolpropane was conducted in a 2 l four-neck flask equipped with stirrer, internal thermometer and two dropwise addition vessels.

The experimental data in Table 1 show that the FA concentration and the FA equivalents added have a crucial influence on the selectivity of the reaction. If Example 1 is compared with Example 2 which was conducted with a lower aldehyde/FA equivalents ratio, a distinctly lower total proportion of desired TMP is found when a smaller aldehyde/FA equivalents ratio is used (Example 2). A minor influence of the reaction temperature becomes clear by comparison with Example 1 with 1.1. With an increase in the reaction temperature, the yield of TMP decreases. Similar results are also obtained in the comparison of example 3.1 with 4.

The influence of the FA concentration is apparent, for example, via comparison of Example 1 with Example 5. In this context, the change in the KOH equivalents plays only a minor role. In Example 5, FA concentration of 25% by weight was used. This FA concentration leads, in spite of twice as long a reaction time, to a TMP content of only 86.3% by weight. An increase in the FA concentration to 36% by weight (Example 3) leads to a further decrease in the TMP content. An excessive proportion of potassium hydroxide has an adverse effect on the TMP yield determined, as can be seen from Example 4. This is also apparent with reference to the results of Example 3.1.

For a high selectivity in the TMP preparation, a low formalin concentration and a high excess of formalin equivalents are favourable. Lower reaction temperatures additionally appear to lead to higher selectivities. In the case of use of higher formalin concentrations, the use of higher KOH equivalents may simultaneously be advantageous. Overall, this mode of operation can achieve selectivities in the region of >89 mol %.

II. Examples 6-10—Individual Batchwise Preparation of NPG (Flask)

The Cannizzaro reaction for preparation of NPG was conducted in a 2 l four-neck flask equipped with stirrer, internal thermometer and two dropwise addition vessels.

The flask was initially charged in accordance with the equivalents of FA specified in Table 2, and the i-butanal and the potassium hydroxide (45% solution) were added uniformly over a period of 10 minutes in accordance with the equivalents given in Table 2 while stirring. By means of the internal thermometer, the reaction temperature was monitored and, if required, kept at the reaction temperature specified with a cold bath (water/ice mixture). After the reaction time specified in Table 2, the reaction is ended by means of addition of formic acid or acetic acid and adjusted to a pH of 6. The respective reaction conditions and the results of the product analysis are listed in Table 2.

TABLE 2

| Example | 6 | 7 | 8 | 9 | 10 |
|---|---|---|---|---|---|
| Reactor | | | Flask | | |
| FA (% by wt.) | 30 | 30 | 34 | 40 | 49 |
| FA eq. | 2.5 | 5 | 3 | 2.5 | 3.5 |
| KOH eq. | 1.1 | 1.1 | 1.2 | 1.1 | 1.45 |
| i-Butanal eq. | | | 1 | | |
| Reaction time [h] | 6 | 6 | 4 | 1 | 0.25 |
| T [° C.] | 60 | 60 | 55 | 55 | 55 |
| Stopping via addition of | CHOOH | CH3COOH | | CHOOH | |
| Product analysis by gas chromatography (% by weight) | | | | | |
| Methanol | 5.76 | 7.48 | 6.1 | 3.24 | 4.73 |
| i- + n-Butanal | 0.00 | 0.02 | 0.01 | 0.02 | 0 |
| Secondary components | 0.72 | 1.5 | 0.21 | 0.18 | 0.56 |
| Hydroxypivaldehyde | 0.00 | 2.34 | 0.01 | 0 | 0.01 |
| NPG | 91.68 | 88.06 | 93.57 | 96.22 | 94.11 |
| High boilers | 1.84 | 0.6 | 0.1 | 0.34 | 0.59 |
| NPG selectivity (%) | 97.5 | 98.4 | 99.7 | 99.5 | 99.0 |

Examples 6-10 demonstrate that the performance of the Cannizzaro reaction in the presence of a large excess of FA with only a low excess proportion of base leads to a relatively low neopentyl glycol content (comparison of Examples 6 and 7). Very long reaction times also have a great influence on the neopentyl glycol content found, as can be seen in Examples 6 and 7, by comparison with examples 9 and 10. In general, for a high selectivity, comparatively higher concentrations of FA solution can be used than in the preparation of trimethylolpropane.

By comparison with the TMP synthesis, the NPG preparation of the invention is also very selective with use of higher formalin concentrations. With 3 to 3.5 formalin equivalents, very good selectivities of >98 mol % are obtained. It can likewise be advantageous also to increase the amount of KOH equivalents in the case of use of higher amounts of formalin.

III. Examples 11-11.1—NPG/TMP Batchwise (Flask)—Simultaneous Mode

The Cannizzaro-reaction for simultaneous preparation of neopentyl glycol and trimethylolpropane was conducted in a 2 l four-neck flask equipped with stirrer, internal thermometer and two dropwise addition vessels.

The flask was initially charged in accordance with the equivalents of FA specified in Table 3, and a mixture of the two n- and i-butanal reactants via a dropping funnel and potassium hydroxide (45% solution) in accordance with the equivalents given in Table 3 via a separate dropping funnel were added uniformly over a period of 10 minutes while stirring. By means of the internal thermometer, the reaction temperature is monitored and, if required, kept at the reaction temperature specified with a cold bath (water/ice mixture). After the reaction time specified in Table 3, the reaction is ended by means of addition of formic acid and adjusted to a pH of 6. The respective reaction conditions and the results of the product analysis are listed in Table 3 together with the results of Examples 12-14 and are also discussed there.

IV. Examples 12-14—NPG/TMP Separate Continuous Addition, Stirred Tank Cascade The continuous and simultaneous Cannizzaro reaction for preparation of NPG and TMP was conducted in a stirred tank cascade with two 1 l reactors, each of which was equipped with a stirrer, internal thermometer, overflow, internal baffles, and inlets with delivery pumps for the n-butanal, i-butanal, potassium hydroxide solution or/and formalin feedstocks.

The first reactor was initially charged, via an immersed tube, with the appropriate total amount of formalin (6.6 equivalents based on n-butanal) and, via a second immersed tube with a crosspiece, with the appropriate equivalents of n-butanal and potassium hydroxide. Via the height of the overflow in the first reactor, it was possible to adjust the fill height and hence the appropriate residence time, as specified in Table 3.

The product removed at the overflow of the first reactor was guided into the second reactor in which, as required, isobutanal and potassium hydroxide solution were added in accordance with Table 3. The residence time in this reactor was again adjusted via an immersed tube.

TABLE 3

| Example | 11 | 11.1 | 12 | 13 | 14 |
|---|---|---|---|---|---|
| Reactor | Flask | | Stirred tank cascade | | |
| FA (% by wt.) | | | 25 | | |
| FA eq. | | | 6.6 | | |
| KOH eq. 1st/2nd stage | 2.2 | 2.2 | 2.2/0 | 1/1.2 | 0.7/1.5 |
| n-Butanal eq. | | | 1 | | |
| i-Butanal eq. | | | 1 | | |
| Reaction time [h] | 1* | 2* | | 2* | |
| T [° C.] 1st/2nd stage | 55 | 55/60 | 50/60 | 50/60 | 50/60 |
| Stopping via addition of | | CHOOH | | | CH3COOH |
| Product analysis by gas chromatography (% by weight) | | | | | |
| Methanol | 2.48 | 2.17 | 19.92 | 5.4 | 8.08 |
| i- + n-Butanal | 0.16 | 0.08 | 0.13 | 0 | 0.27 |
| Secondary components | 0.20 | 1.13 | 2.97 | 0.64 | 0.54 |
| Hydroxypivaldehyde | 0.00 | 0.00 | 0.94 | 0.67 | 0.58 |
| NPG | 44.79 | 42.72 | 13.38 | 42.65 | 34.25 |
| TMP | 45.56 | 47.05 | 24.47 | 41.57 | 42.93 |
| Formates/intermediate fractions | 3.56 | 3.48 | 36.94 | 4.97 | 9.63 |
| Di-TMP | 1.12 | 1.03 | 0.36 | 1.01 | 1.17 |
| Linear bis-TMP formal | 1.74 | 1.61 | 0.59 | 2.69 | 1.91 |

TABLE 3-continued

| Example | 11 | 11.1 | 12 | 13 | 14 |
|---|---|---|---|---|---|
| High boilers | 0.39 | 0.73 | 0.3 | 0.4 | 0.64 |
| TMP selectivity (%) | 87.9 | 89.4 | 53.8 | 88.4 | 84.2 |
| NPG selectivity (%) | 99.3 | 97.0 | 52.7 | 91.3 | 86.9 |

*= total reaction time as a sum total of the TMP and NPG stages

It has been found that, in a stirred tank cascade, the two desired products can in principle be prepared with exploitation of an FA excess, but increased occurrence of formates and intermediate fractions was also recorded by comparison with the simultaneous preparation in a one-pot process (Examples 11-11.1). This can be seen from the selectivities reported, which are already within the target range for TMP (~89%) and NPG (~98%).

V. Examples 15-18—NPG/TMP Separate Addition, Batchwise, Flask

The Cannizzaro reaction for preparation of neopentyl glycol and trimethylolpropane was conducted in a 2 l four-neck flask equipped with stirrer, internal thermometer and two dropwise addition vessels.

First of all, analogously to Examples 1 to 5, trimethylolpropane was prepared. For this purpose, the appropriate amount of formalin (6.6 equivalents based on n-butanal) according to Table 4 was initially charged, and n-butanal and base (potassium hydroxide/NaOH, >40% solution) in accordance with the equivalents specified in Table 4 were added uniformly over a period of 10 minutes while stirring. By means of the internal thermometer, the reaction temperature is monitored and, if required, kept at the reaction temperature specified with a cold bath (water/ice mixture). In the 2nd stage, after half the reaction time specified in Table 4, an appropriate amount of i-butanal and, if appropriate, potassium hydroxide/sodium hydroxide solution is added within 10 minutes and the mixture is stirred for a further half of the reaction time specified. The reaction is ended by means of addition of formic acid or acetic acid and adjusted to a pH of 6. The respective reaction conditions and the results of the product analysis are listed in Table 4.

TABLE 4

| Example | 11.1 | 15 | 16 | 17 | 18 |
|---|---|---|---|---|---|
| Reactor | | | Flask | | |
| FA (% by wt.) | 25 | 30 | | 25 | |
| FA eq. | | | 6.6 | | |
| Base | | KOH | | | NaOH |
| Bases eq. lst/2nd stage | 2.2 | 2.2/0 | 1.1/1.1 | 1.1/1.1 | 1.1/1.1 |
| n-Butanal eq. | | | 1 | | |
| i-Butanal eq. | | | 1 | | |
| Reaction time [h] | | | 2* | | |
| T [° C.] lst/2nd stage | 55/60 | 40/50 | 60/60 | 55/60 | 55/60 |
| Stopping via addition of | | CHOOH | | | CH3COOH |
| Product analysis by gas chromatography (% by weight) | | | | | |
| Methanol | 2.17 | 9.36 | 3.47 | 2.93 | 2.96 |
| i- + n-Butanal | 0.08 | 6.57 | 0.3 | 0.11 | 0 |
| Secondary components | 1.13 | 0.18 | 0.42 | 0.27 | 0.56 |
| Hydroxypivaldehyde | 0.00 | 13.98 | 0 | 0 | 0 |
| NPG | 42.72 | 12.16 | 49.05 | 49.46 | 45.64 |
| TMP | 47.05 | 51.28 | 43.21 | 44.8 | 45.71 |
| Formates/intermediate fractions | 3.48 | 4.17 | 1.4 | 0.76 | 1.22 |
| Di-TMP | 1.03 | 0.33 | 0.3 | 0.22 | 0.86 |
| Linear bis-TMP formal | 1.61 | 0.66 | 1.24 | 0.58 | 2 |

TABLE 4-continued

| Example | 11.1 | 15 | 16 | 17 | 18 |
|---|---|---|---|---|---|
| High boilers | 0.73 | 1.31 | 0.61 | 0.87 | 1.05 |
| TMP selectivity (%) | 89.42 | 95.07 | 94.56 | 96.33 | 92.15 |
| NPG selectivity (%) | 97.01 | 80.16 | 97.13 | 98.22 | 96.55 |

*= total reaction time as a sum total of the TMP and NPG stages

A reaction solution having a high product content of neopentyl glycol and trimethylolpropane is obtained, for example, via the reaction conditions of Example 17. More particularly, it should be emphasized that it was possible to lower the proportion of formates/intermediate fractions in this example to a value below 1% by weight. In addition, it was found, advantageously, that the necessary amount of base is added in the appropriate reaction stage in each case (compare Example 15 with Examples 16-18).

If example 11.1 is compared with Examples 15-18, a significantly higher selectivity for TMP is found for Examples 15-18. Taking account of experiments 1-5 (TMP synthesis only), a selectivity advantage is unexpectedly apparent for examples with a consecutive TMP/NPG mode of operation. This may be caused by reduced formation of linear TMP formals and is a clear indication of the advantageousness of a consecutive mode of operation. In the optimized experimental settings of Examples 17 and 18, it is possible to achieve NPG selectivities just as good as in Example 11.1.

VI. Examples 19-22—NPG/TMP Separate Continuous Addition, Tubular Reactor

The Cannizzaro reaction for coupled preparation of neopentyl glycol and trimethylolpropane was conducted in a tubular reactor having a length of 175 m and an internal tubular diameter of 3 mm. The entire tube is divided into two tubular reactor sections, each of which was set to the desired reaction temperature with the aid of a heating bath.

The reactants were added via crosspieces in the tubular reactor inlet. The total amount of FA was fed in at the start of the tubular reactor. To increase the yield of trimethylolpropane, the addition of n-butanal and potassium hydroxide/sodium hydroxide in the trimethylolpropane reaction stage (1st reactor section) was optionally effected stepwise (compare Examples 19 and 22). Upstream of the second reactor tube section, i-butanal and potassium hydroxide/sodium hydroxide solution were then metered in, such that neopentyl glycol forms through consumption of the excess formalin in the second tubular reactor section. Samples are taken from the collecting vessels and the reaction is quenched with formic acid. The respective reaction conditions and the results of the product analysis are listed in Table 5.

TABLE 5

| Example | 19 | 20 | 21 | 22 |
|---|---|---|---|---|
| Reactor | | Tube | | |
| FA (% by wt.) | | 25 | | |
| FA eq. | | 6.6 | | |
| Base | | KOH | | |
| Bases eq. lst/2nd stage | | 1.1/1.1 | | |
| n-Butanal eq. | 1 | | | 1 (grad.) |
| i-Butanal eq. | | 1 | | |
| Residence time [min] | | 40 | | |
| T [° C.] lst/2nd stage | 40/60 | 50/50 | 20/30 | 40/60 |
| Stopping via addition of | | CHOOH | | |

TABLE 5-continued

| Example | 19 | 20 | 21 | 22 |
|---|---|---|---|---|
| Product analysis by gas chromatography (% by weight) | | | | |
| Methanol | 4.39 | 3.30 | 2.18 | 3.10 |
| i- +n-Butanal | 0.17 | 0.14 | 0.15 | 0.03 |
| Secondary components | 2.17 | 0.73 | 2.14 | 0.70 |
| Hydroxypivaldehyde | 0 | 0 | 0 | 0 |
| NPG | 42.39 | 48.29 | 44.21 | 44.33 |
| TMP | 49.28 | 46.43 | 50.27 | 51.01 |
| Formates/intermediate fractions | 2.17 | 0.61 | 2.14 | 0.70 |
| Di-TMP | 0.20 | 0.01 | 0.00 | 0.09 |
| n bis-TMP formal | 0.04 | 0.35 | 0.00 | 0.01 |
| High boilers | 0.49 | 0.50 | 0.09 | 0.20 |
| TMP selectivity (%) | 92.87 | 96.34 | 93.92 | 97.59 |
| NPG selectivity (%) | 95.28 | 98.13 | 95.89 | 98.47 |

*= total reaction time as a sum total of the TMP and NPG stages;
(grad.) = gradual addition of n-butanal The comparison of the product analysis for TMP and NPG (experiments 19-22) shows that results comparably good to those in the flask reactor can be achieved (experiments 15-18). The conversion of a batchwise flask experiment to the continuous mode of operation corresponds to performance in a tubular reactor with stepwise addition. In addition, in the first process step, with simple addition, a selectivity of 92.9-96.3% for TMP and 95.3-98.1% for NPG can be achieved (experiments 19-21). By comparison, Example 22 shows the positive effect of stepwise addition of the n-butanal. Through the stepwise addition of n-butanal in the first reaction stage at reduced reaction temperature (40° C.) (experiment 22), excellent selectivities can be achieved for the two TMP (97.6%) and NPG (98.5%) products. The second reaction step can again be conducted at higher temperatures (60° C.) without finding any reduction in the selectivity for both products here. The elevated temperature is conducive to the achievement of full conversion with reduced reaction volume. In all the examples so far, it has not been possible to show, in combination, such a high overall selectivity and accompanying overall yield of TMP and NPG.

VII. Consideration of Energy Saving

The direct effect of the utilization of the unconverted formaldehyde by the 2nd process step is that the stream of excess formaldehyde which is removed after the reaction is smaller. This leads directly to an energy saving, the energy saving and the amount of formaldehyde to be removed being virtually proportional, since formalin leads to a slight lowering of the boiling point.

The energy saving is to be illustrated using an example calculation for the production of 1 kmol of trimethylolpropane and 1 kmol of neopentyl glycol. In the case of use of a formalin solution with 20% by weight of trimethylolpropane and 35% by weight of neopentyl glycol with the respective equivalents as specified in Table 6, the mass flow rate of water and formalin is 1257 kg, which has to be removed after the end of the reaction in the case of a batchwise mode of operation, whereas, in the case of a consecutive simultaneous mode of operation with an FA solution of 20% by weight, only 957 kg are obtained. In the case of use of 30 bar heating steam and taking note of the energy present therein, there is ultimately an energy saving of 24%. In the consecutive simultaneous mode of operation, about 1.2 eq. of unreacted formaldehyde (3.8% by mass) remain at the end, whereas, in a separate batchwise preparation, there remain 4.7 eq. of formaldehyde (3.4 eq. in the case of TMP and 1.3 eq. in the case of NPG) (11.9% by mass).

TABLE 6

| Mode of operation | Separate preparation TMP: 20% by wt. of formalin, 6.6 eq. NPG: 35% by wt. of formalin, 3.5 eq. | Coupled preparation. 20% by wt. of formalin, 6.6 eq |
|---|---|---|
| Mass flow rate of H2O + FA/kg | 1257 | 957 |
| Energy required/kJ (mass flow rate × spec. enthalpy of evaporation) | $2.54 \cdot 10^6$ | $2.04 \cdot 10^6$ |
| Difference in % | 24 | |

The invention claimed is:

1. A process for simultaneously consecutive preparation of at least two different polyols by reaction of aliphatic aldehydes with formaldehyde in the presence of an inorganic base, characterized in that, in a 1st process step, an aliphatic C2-C9 aldehyde is reacted with formaldehyde in the presence of an inorganic base and, without workup of the reaction solution, in a 2nd process step, the reaction solution from the 1st process step is converted further with addition of at least one aliphatic C2-C9 aldehyde other than the aldehyde from the 1st process step.

2. The process according to claim 1, wherein, in the 1st process step, an aliphatic C2-C9 aldehyde unbranched in the 2 position is reacted, and, in the 2nd process step, an aliphatic C2-C9 aldehyde branched in the 2 position.

3. The process according to claim 1, wherein the aldehyde used in the 1st process step is selected from the group consisting of n-propanal, n-butanal, valeraldehyde, and the aldehyde used in the 2nd process step is i-butanal.

4. The process according to claim 1, wherein the 1st and 2nd process step are conducted at a temperature of greater than or equal 10° C. and less than or equal 105° C.

5. The process according to claim 1, wherein, in the 2nd process step, an inorganic base is additionally added to the reaction solution.

6. The process according to claim 5, wherein the same inorganic base is used in the 1st and 2nd process step.

7. The process according to claim 1, wherein the inorganic base is selected from the group consisting of NaOH, KOH, Ca(OH)$_2$ or mixtures thereof.

8. The process according to claim 1, wherein the molar ratio of inorganic base to aliphatic aldehyde in the two process steps is greater than or equal 1:1 and less than or equal 1.6:1.

9. The process according to claim 1, wherein the formaldehyde is added in the 1st process step in the form of an aqueous formaldehyde solution having a formaldehyde content of greater than or equal 5% by weight and less than or equal 50% by weight.

10. The process according to claim 1, wherein the molar ratio of formaldehyde to aliphatic aldehyde in the first process step is greater than or equal 3.1:1 and less than or equal 12:1 and the molar ratio of formaldehyde to aliphatic aldehyde in the 2nd process step is greater than or equal 2.1:1 and less than or equal 7:1.

11. The process according to claim 1, wherein formaldehyde is added only in the 1st process step.

12. The process according to claim 1, wherein the addition of at least one reactant in the 1st and/or in the 2nd process step is effected stepwise.

13. The process according to claim 12, wherein the aliphatic aldehyde in the 1st process step is added stepwise to the reaction mixture.

14. The process according to claim 1, wherein the conversion of aldehyde in the reaction mixture at the end of the 1st process step is greater than or equal 50%.

15. The process according to claim 1, wherein the reactant volume throughput per unit reactor volume and time (V/Vh) in the two process steps is greater than or equal 0.3 and less than or equal 4.0.

16. The process according to claim 2, wherein an inorganic base is additionally added to the reaction solution in the 2nd process step.

17. The process according to claim 2, wherein the molar ratio of inorganic base to aliphatic aldehyde in the two process steps is greater than or equal 1:1 and less than or equal 1.6:1.

18. The process according to claim 2, wherein formaldehyde is added only in the 1st process step.

19. The process according to claim 2, wherein the aliphatic aldehyde in the 1st process step is added stepwise to the reaction mixture.

20. The process according to claim 1, wherein formaldehyde is added only in the 1st process step; the aliphatic aldehyde in the 1st process step is selected from the group consisting of n-propanal, n-butanal, and valeraldehyde and is added stepwise to the reaction mixture; the aliphatic aldehyde in the $2^{nd}$ process step is i-butanal; an inorganic base is additionally added to the reaction solution in the 2nd process step; the molar ratio of inorganic base to aliphatic aldehyde in the two process steps is greater than or equal 1:1 and less than or equal 1.6:1; and the reactant volume throughput per unit reactor volume and time (V/Vh) in the two process steps is greater than or equal 0.3 and less than or equal 4.0.

* * * * *